(12) United States Patent
Gunnesch et al.

(10) Patent No.: US 12,661,423 B2
(45) Date of Patent: Jun. 23, 2026

(54) SYSTEM FOR CONVEYING A STERILIZATION MEDIUM AND METHOD OF PROVIDING A STERILIZATION MEDIUM

(71) Applicant: BUERKERT WERKE GMBH & CO. KG, Ingelfingen (DE)

(72) Inventors: Johann Gunnesch, Ingelfingen (DE); Alexej Iwaschkin, Ingelfingen (DE); Harald Schaefer, Ingelfingen (DE)

(73) Assignee: Buerkert Werke Gmbh & Co. KG, Ingelfingen (DE)

( * ) Notice: Subject to any disclaimer, the term of this patent is extended or adjusted under 35 U.S.C. 154(b) by 413 days.

(21) Appl. No.: 18/410,561

(22) Filed: Jan. 11, 2024

(65) Prior Publication Data

US 2024/0238467 A1 Jul. 18, 2024

(30) Foreign Application Priority Data

Jan. 16, 2023 (DE) .......................... 102023100887.0

(51) Int. Cl.
*A61L 2/26* (2006.01)
*A61L 2/208* (2026.01)
(Continued)

(52) U.S. Cl.
CPC ................. *A61L 2/26* (2013.01); *A61L 2/208* (2013.01); *A61L 2/18* (2013.01); *A61L 2/22* (2013.01);
(Continued)

(58) Field of Classification Search
CPC ... A61L 2/26; A61L 2/208; A61L 2/18; A61L 2/186; A61L 2/22; A61L 2/24; A61L 2202/15; A61L 2202/17; A61L 2202/14
(Continued)

(56) References Cited

U.S. PATENT DOCUMENTS 3,131,708 A * 5/1964 Knight .................. F17C 13/045
137/113
4,341,234 A * 7/1982 Meinass ................ F17C 13/045
137/113
(Continued)

FOREIGN PATENT DOCUMENTS

CN 114588843 A 6/2022
WO 2011139300 A2 11/2011

*Primary Examiner* — Minh Q Le

(74) *Attorney, Agent, or Firm* — McNees Wallace & Nurick LLC

(57) ABSTRACT

A system for conveying a sterilization medium comprises at least two buffer containers for sterilization medium which are arranged so as to be connected in parallel, at least one fluid flow controller, to which each of the buffer containers is fluidically coupled, and a pressure media supply device, which couples a pressure medium source to the buffer containers and is adapted to act upon the buffer containers with a pressure medium. The system is configured such that for each buffer container a fill mode and a spray mode can be set. In the fill mode the correspondingly switched buffer container is adapted to be filled with the sterilization medium from a supply device, and in the spray mode the correspondingly switched buffer container is fluidically coupled to the fluid flow controller and the sterilization medium can be conveyed from this buffer container toward the fluid flow controller based on a pressure applied by the pressure medium. The buffer containers are adapted to be switched alternately.

12 Claims, 2 Drawing Sheets

(51) Int. Cl.
  *A61L 2/18* (2006.01)
  *A61L 2/22* (2006.01)
  *A61L 2/24* (2006.01)

(52) U.S. Cl.
  CPC ............. *A61L 2/24* (2013.01); *A61L 2202/14* (2013.01); *A61L 2202/15* (2013.01); *A61L 2202/17* (2013.01)

(58) Field of Classification Search
  USPC ..................................... 137/806, 7, 815, 113
  See application file for complete search history.

(56) References Cited

U.S. PATENT DOCUMENTS

| | | | | | |
|---|---|---|---|---|---|
| 4,380,242 | A | * | 4/1983 | Bresie | F17C 13/045 137/565.13 |
| 4,597,406 | A | * | 7/1986 | Loiseau | F17C 13/045 137/113 |
| 5,129,415 | A | * | 7/1992 | Runyon | C02F 1/686 210/101 |
| 5,502,685 | A | * | 3/1996 | Orlando | A01M 7/0092 366/132 |
| 5,777,213 | A | * | 7/1998 | Tsukazaki | B01D 15/08 137/7 |
| 6,105,598 | A | * | 8/2000 | Cabrera | F17C 13/04 137/907 |
| 6,962,627 | B2 | * | 11/2005 | Sekiguchi | B05C 11/1002 222/64 |
| 7,201,178 | B2 | * | 4/2007 | Gupta | G05D 7/0635 137/434 |
| 8,479,951 | B2 | * | 7/2013 | Ciavarella | A47K 5/14 222/66 |
| 12,584,777 | B2 | * | 3/2026 | Reuter | G01F 13/006 |
| 2006/0047186 | A1 | | 3/2006 | Annecke | |
| 2006/0130896 | A1 | * | 6/2006 | Skibinski | F17C 7/00 137/7 |
| 2014/0014742 | A1 | * | 1/2014 | Kruger | C23C 16/56 137/7 |
| 2016/0250365 | A1 | | 9/2016 | Mo et al. | |
| 2022/0001058 | A1 | * | 1/2022 | Matsuo | A61L 2/202 |
| 2022/0047749 | A1 | * | 2/2022 | Birch | A61L 2/26 |
| 2022/0264864 | A1 | | 8/2022 | Sandey et al. | |
| 2023/0309544 | A1 | * | 10/2023 | Charillon | A01M 13/00 43/125 |

* cited by examiner

68 system in operation = one buffer container always in spray mode

14a buffer container 1

14b buffer container 2

Figure 2:
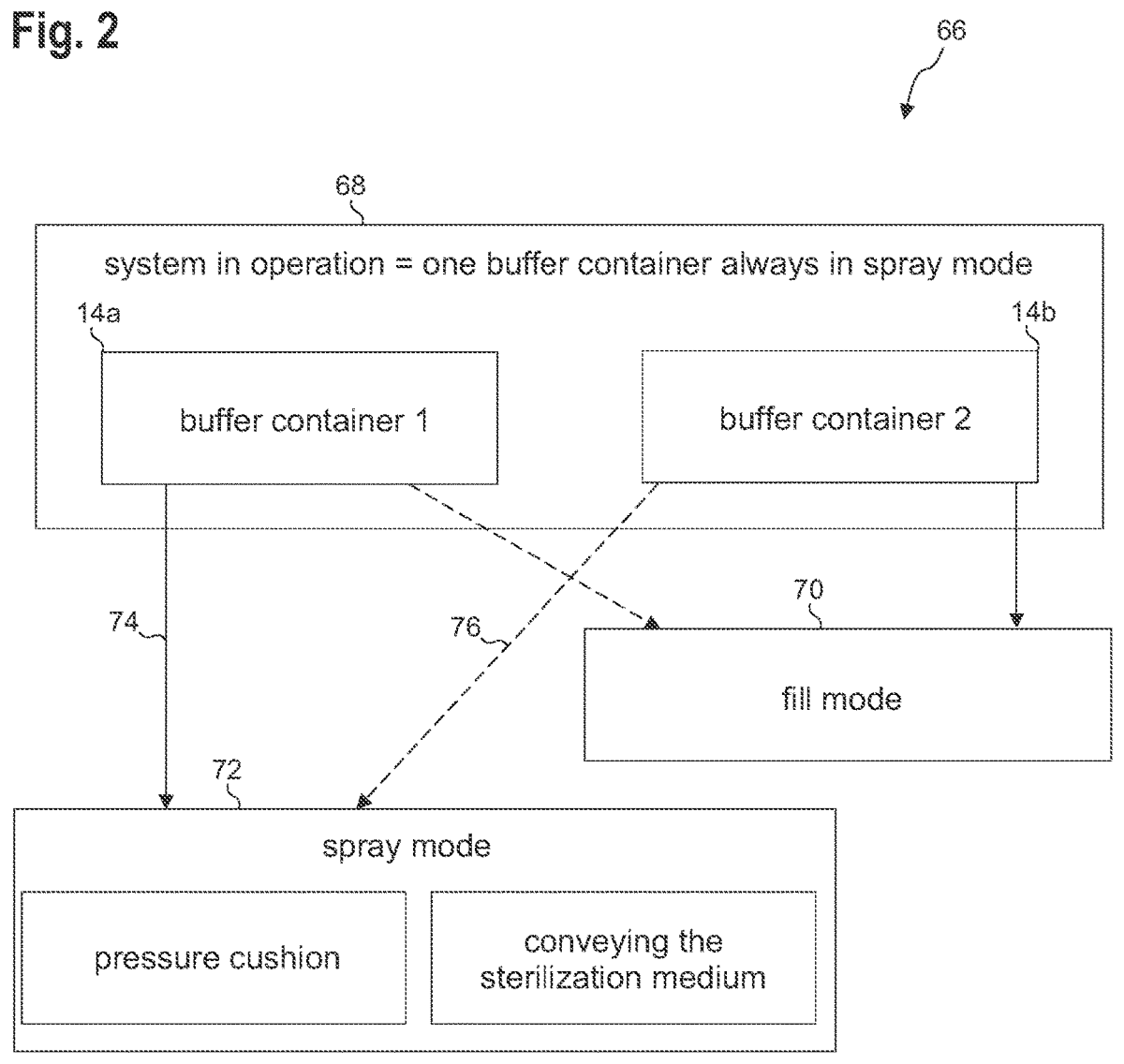

74

76

70 fill mode

72 spray mode pressure cushion conveying the
sterilization medium

SYSTEM FOR CONVEYING A STERILIZATION MEDIUM AND METHOD OF PROVIDING A STERILIZATION MEDIUM

TECHNICAL FIELD

The present disclosure relates to a system for conveying a sterilization medium and to a method of providing a sterilization medium.

BACKGROUND

Nowadays, food packaging and other objects are frequently subjected to sterilization media (for example hydrogen peroxide) in order to remove germs and bacteria therefrom. Since the sterilization media are often aggressive (for example corrosive), specialized peristaltic pumps are employed for delivery here. However, due to the contact with the sterilization medium, these peristaltic pumps require particularly high maintenance, which increases the operating expenditure.

Moreover, peristaltic pumps cause a pulsation of the sterilization medium delivered, which results in an increased outgassing of the sterilization medium. Furthermore, the pulsation prevents the sterilization medium from flowing evenly and continuously. In particular, flow measurement and flow control are adversely affected, as a result of which the precision of the sterilization process is also reduced.

In addition, known systems often employ buffer tanks that have to be refilled again after the respective buffered quantity of sterilization medium has been consumed. This causes additional interruptions to the sterilization process.

As an alternative, ring circuit systems are also known, in which an object to be sterilized is acted upon by the sterilization medium. The sterilization medium is subsequently recovered through a ring circuit topology of the supply circuit. However, such ring circuit systems also lead to increased outgassing of the sterilization medium from the system and require complex filter devices to ensure a predetermined concentration of the sterilization medium.

The present disclosure to able remove or at least reduce the drawbacks of the prior art. In particular, there is a need to provide a system and a method by means of which a continuous, uninterrupted metering of a sterilization medium is made possible.

SUMMARY

According to one aspect, a system for conveying a sterilization medium is provided. The system comprises at least two buffer containers arranged so as to be connected in parallel, for storing the sterilization medium, at least one fluid flow controller, to which each of the buffer containers is fluidically coupled, and a pressure media supply device. The pressure media supply device couples a pressure medium source to the buffer containers and is adapted to act upon the buffer containers with a pressure medium. The system is configured such that for each buffer container a fill mode and a spray mode can be set. In the fill mode the correspondingly switched buffer container is adapted to be filled with the sterilization medium from a supply device. In the spray mode the correspondingly switched buffer container is fluidically coupled to the fluid flow controller and the sterilization medium can be conveyed from this buffer container toward the fluid flow controller based on a pressure applied by the pressure medium. The buffer containers are adapted to be switched alternately, so that while one container is in the spray mode, the other or another buffer container is in the fill mode.

The present system provides a multitude of advantages. The system advantageously does not require any pumps to convey the sterilization medium; it is pumpless with regard to the sterilization medium. Conveyance of the sterilization medium is made possible by means of a pressure cushion provided by the pressure medium. This allows the operating efficiency to be increased, because the high-maintenance special pumps for such sterilization media are no longer required.

Moreover, doing without peristaltic pumps means that the sterilization medium is conveyed without pulsation. This allows the sterilization medium to flow continuously and evenly. In particular, this also improves the precision of flow rate determination and flow control, since the sterilization medium can be provided at a constant volume flow rate.

Avoiding pulsation (no pressure surges) also results in less outgassing of the sterilization medium from the system, so that the losses of sterilization medium are reduced.

In addition, there is an improvement in the flexibility of providing the sterilization medium. Peristaltic pumps for such sterilization media usually have fixed delivery parameters. This means that the sterilization medium can only be provided at fixed flow rates. In the present case, in contrast, the flow rate of the sterilization medium can be adjusted as necessary by using a pressure cushion. This allows the sterilization medium to be metered over a wide parameter range, depending on the requirements of the downstream flow control.

Since the system comprises two buffer containers that can be selectively switched between the fill mode and the spray mode, it is more particularly possible to switch over from one buffer container, for which the spray mode is set, to the second buffer container in the spray mode without interruption. This allows continuous metering of the sterilization medium. In other words, during operation of the system, the spray mode can optionally always be set for at least one buffer container.

It is solely during the switchover from one buffer container in spray mode to another buffer container in spray mode that the system may show a one-time negligible short interference pulse. But during the provision of the sterilization medium from a respective buffer container, the system does not exhibit any pulsation during operation. As such, the system may also be referred to as quasi-pulsation-free.

In the present case, the system is also not designed as a ring circuit, in which the sterilization medium is recovered. In this respect, too, the outgassing of the sterilization medium from the system is therefore reduced in comparison to known ring circuit systems. Furthermore, complex filter devices may be avoided, which are required in known ring circuit systems in order to ensure the purity and concentration of the sterilization medium.

In addition, the system can be modularly extended depending on requirements. For example, additional buffer containers or aerosol outlets may be provided. Furthermore, the tank volume of one or more buffer containers may be adapted as required.

Optionally, it is also possible to provide a plurality of fluid flow controllers to which the respective buffer containers arranged in parallel are fluidically coupled. In this way, defined fluid flows can be provided as required for different aerosol outlets.

The system therefore allows a high degree of flexibility, a reduction in outgassing of the sterilization medium, and an advantageously improved, more even supply of the sterilization medium by means of a pressure cushion, and avoidance of pulsation. Thus, both flow rate determination and flow control are possible with increased precision.

According to a further aspect, a method of providing a sterilization medium by means of a system as described above is also provided. If the fill mode is set for a buffer container, this buffer container is filled with the sterilization medium from a supply device. If the spray mode is set for a buffer container, this buffer container is acted upon with the pressure medium starting from the pressure media supply device such that a pressure is generated in the buffer container. This buffer container is then additionally fluidically coupled to the fluid flow controller. Furthermore, based on the pressure generated by the pressure medium within the buffer container, sterilization medium is conveyed from this buffer container toward the fluid flow controller. The system can be switched such that during operation of the system, the spray mode can always be set for at least one buffer container.

The advantages that are achieved by the system according to the disclosure are likewise achieved by the method in a corresponding manner.

In the present case, a sterilization medium is to be understood to be a medium that can be used to remove germs and bacteria or living organisms from an object. Optionally, the sterilization medium is liquid.

In the present case, the pressure media supply device may be understood to be a part of the system, a complex device or a subsystem that is configured to provide a pressure medium. To this end, the pressure media supply device may include its own valves, storage reservoirs, conveying pipes and other components relevant in terms of pressure technology.

In the present case, the pressure medium may be understood to be a medium that is suitable for generating a pressure cushion with respect to the sterilization medium stored in the buffer containers. The pressure medium may be in liquid or gaseous form in the buffer containers, preferably gaseous.

Optionally, the pressure medium may be such that no mixing with the sterilization medium takes place, or only negligible mixing.

In some embodiments, the pressure medium may comprise compressed air.

The fluid flow controller may be configured to adjust a volume flow of the sterilization medium in accordance with a predefined setpoint value.

In the present case, the supply device may be understood to be a higher-level device or a superordinate system, from which the individual buffer containers can be filled with the sterilization medium. For example, the supply device may include a main tank for the sterilization medium, to which the system is coupled with respect to the sterilization medium. In addition, the supply device may also include a supply network via which the sterilization medium can be provided.

The buffer containers may also be switchable in such a way that they can be filled simultaneously, that is, they are in the fill mode at the same time. This is advantageous, for example, for an initial filling of the system, since nominal target filling levels of the sterilization medium can then be reached simultaneously for all buffer containers.

Optionally, atmospheric pressure prevails in the buffer container for which the fill mode is set. This further improves the flexibility of the system. Since the buffer containers are filled against atmospheric pressure, each buffer container can be filled in accordance with a preselected filling level depending on requirements. For example, the filling process may thus also be carried out based on utilization of the geodetic height. In addition, the sterilization medium does not need to be filled into the respective buffer container under pressure.

In some embodiments, each buffer container is coupled to a respective mechanical or electronic pressure measuring device. In particular, the pressure measuring device may be configured to determine the fluid pressure within the respective buffer container. The information may be used to provide automation of the conveyance of the sterilization medium.

The pressure measuring device may alternatively or cumulatively also be configured to determine the gas pressure above a quantity of fluid in the respective buffer container. The gas pressure may, for example, be applied by the pressure medium here.

Optionally, the pressure measuring device may also comprise, or be coupled to, a pressure transmitter. The pressure determined in each case can then be transmitted to a higher-level control device of the system using the pressure transmitter. This simplifies control regarding the conveyance of the sterilization medium and the pressure medium.

Each buffer container may include at least one filling level meter. The filling level meter may further be configured to transmit the respectively determined filling level to a control device of the system. Based on the filling level of the respective buffer container, the control of the conveyance of the sterilization medium is simplified.

In some embodiments, the system further includes a mechanical or electronic pressure regulating device. The pressure regulating device is coupled at least to the buffer containers and to the pressure media supply device and is configured to act upon each buffer container with a predefined pressure based on the pressure medium. In particular, the predefined pressure, which is ensured by the pressure regulating device with respect to the pressure medium within the respective buffer container, may be variable. Since the pressure cushion provided by the pressure medium ensures the conveyance of the sterilization medium, a variable conveyance rate of the sterilization medium can in this way be provided in an advantageously simple manner.

Optionally, the pressure regulating device is at least indirectly coupled to a pressure measuring device of the respective buffer container. For example, both the pressure measuring device and the pressure regulating device may be coupled to a higher-level control device of the system. The control device controls the pressure regulating device and thus the conveyance of the pressure medium in such a way that a desired pressure of the pressure medium in the respective buffer container is ensured as a pressure cushion above the sterilization medium.

The pressure regulation may also be executed as a computer program using the control device, which may include an appropriate data processing device for this purpose and controls a pressure regulator accordingly.

For each buffer container, the system may include a proportional valve between the pressure regulating device and the buffer containers. This allows a control loop, by means of which the pressure cushion is ensured using the pressure medium above the sterilization medium within a buffer container, to take more complex control mechanisms into account. A proportional valve, for example, enables a PID (proportional-integral-derivative) control. This improves the control action. For example, the control mechanism may be carried out by a higher-level control device of the system, which appropriately controls the proportional valve and other valves or components of the system.

Optionally, for each buffer container, rather than a proportional valve, a shut-off valve (switching valve; binary-acting valve) may also be arranged between the pressure regulating device and the buffer containers. A shut-off valve may also be sufficient to ensure the pressure cushion on the basis of the pressure medium above the sterilization medium within a respective buffer container.

In some embodiments, only one proportional valve may be arranged respectively between the pressure regulating device and the buffer containers. Optionally, for example to take additional safety mechanisms into account, an additional valve, for example a 3/2-way valve or a shut-off valve, may also be arranged between the pressure regulating device and the respective buffer containers in addition to the proportional valve. This allows the control concept to be adapted to suit the needs with regard to the conveyance of the pressure medium and thus also the sterilization medium.

Optionally, each buffer container is coupled to at least one respective pressure relief valve. Since the sterilization medium expands when transitioning to the gaseous state of aggregation, an additional safety mechanism is provided in this way.

The pressure relief valve can be configured such that the respective buffer container is at atmospheric pressure when the air bleed valve is open. This simplifies the filling process using the pressure relief valve, since it is then possible to fill against atmospheric pressure.

In some embodiments, a non-return valve is arranged between each buffer container and the pressure media supply device such that a return flow from the buffer container into the pressure media supply device is inhibited. This prevents a contamination of the pressure media supply device with the sterilization medium. Furthermore, this allows a set pressure of the pressure cushion, which is generated using the pressure medium provided by the pressure media supply device, to be ensured in a simple manner.

Optionally, the system further includes at least one dual-substance nozzle which, starting from the fluid flow controller, is adapted to be acted upon with the sterilization medium and additionally with a conveying medium. The dual-substance nozzle is arranged to atomize the sterilization medium through the conveying medium. This allows the sterilization medium to be provided for an end application. Advantageously, the atomized volume flow provided by the dual-substance nozzle can be ensured continuously and evenly.

Alternatively, the dual-substance nozzle may also be external to the system. In this case, only the preset volume flow of the sterilization medium is provided downstream in relation to the fluid flow controller.

In some embodiments, provision may also be made for a plurality of dual-substance nozzles, which, starting from the fluid flow controller or controllers, can be acted upon by the sterilization medium and additionally by a conveying medium.

A medium that can also be used as a pressure medium of the system can be used as the conveying medium used by the dual-substance nozzle to atomize the sterilization medium. For example, compressed air may be used both as a pressure medium and as a conveying medium. In this case, the pressure media supply device may be of such a type that the pressure medium is additionally provided as a conveying medium for the dual-substance nozzle.

Optionally, the system further includes a purging device for each buffer container, which is configured to purge the respective buffer container with a cleaning agent.

The cleaning agent may comprise, for example, compressed air or water, such as, e.g., distilled water. Optionally, the cleaning agent may also comprise water with cleaning additives.

In some embodiments, each buffer container has an outlet line that leads to a common line to the fluid flow controller. Provided in the respective outlet lines are shut-off valves which are closed in the fill mode. This allows each buffer container to be disconnected from the fluid flow controller for the fill mode as required.

Optionally, at least one of the shut-off valves that are arranged in the respective outlet lines is constructed to be "normally open". This means that in the absence of a control signal, for example a control voltage or the application of a control fluid above a predetermined limit value, the valve is open. When the respective limit value is exceeded, the valve is closed. This provides an additional safety mechanism.

At least some valves can be pneumatically actuatable valves. In particular, the pressure medium may also be applied to the pneumatically actuatable valves in order to adjust their position. Then only a single additional pressure media supply device is necessary in order to provide both the pressure medium for providing the pressure cushion, the conveying medium for the dual-substance nozzle and also a medium by means of which the valves can be controlled.

Optionally, the system includes a control device. The control device is at least configured to appropriately set the buffer containers to the fill mode or to the spray mode. The control device is further configured to suitably control components of the system so as to make sure that a buffer container is in the fill mode or the spray mode. For example, the control device may drive respective valves. Furthermore, the control device may also be coupled to other components of the system for control purposes, for example pressure measuring devices, pressure transmitters or pressure controllers. Moreover, the control device may also be configured to ensure that the pressure medium is conveyed in accordance with requirements. For example, the control device may also ensure control of the pressure media supply device.

In some embodiments, each buffer container has at least one pressure control valve coupled to it. This produces an additional safety mechanism. The respective pressure control valve may be in the form of a mechanical pressure control valve. This ensures the safety mechanism even in the event of failure of the underlying electronic control system. In particular, this averts the risk in the case of an expanding sterilization medium.

The outlet lines of the respective buffer containers can be coupled to a drainage for disposing of the sterilization medium. This means that the system is not designed as a ring circuit. This reduces the outgassing of the sterilization medium from the system. In addition, a respective buffer container can be emptied in this way, for example for maintenance purposes.

Optionally, the fluid flow controller is directly coupled to the dual-substance nozzle. This means that the fluid flow controller and the dual-substance nozzle may also be combined in one device.

In some embodiments, the system includes additional buffer containers that are fluidically connected in parallel to one of the at least two buffer containers. A group of buffer containers may then provide a single contiguous volume (storage unit) for the sterilization medium. This means that some buffer containers are interconnected to form an individual contiguous volume. However, there are at least two groups of buffer containers or one group of buffer containers and one individual buffer container for which the fill mode or the spray mode can be set separately.

Alternatively or cumulatively, additional buffer containers may also be provided for which the fill mode or the spray mode can be set in addition, parallel to the already existing buffer containers.

Optionally, individual buffer containers may also be disconnected separately, for example for maintenance purposes.

This allows the total volume for the sterilization medium to be adjusted to suit the requirements, for example as a function of the size of the system or the application.

Optionally, the system also includes pressure sensors. For example, each buffer container may have a pressure sensor coupled to it. Furthermore, a pressure sensor may be coupled to a feed line that is arranged between the supply device and the respective buffer container. The pressure sensor may also be adapted to determine a pressure differential, for example with respect to the feed lines to which different buffer containers are coupled. This allows the regulation of the conveyance of the sterilization medium to be improved.

Provision may be made for a pressure measurement for the input of the system in relation to the supply device for the sterilization medium and/or for the input of the pressure media supply device in relation to the pressure medium. That is, pressure measurements may be provided for both the sterilization section and the pressure medium section. This simplifies control for the conveyance of the pressure medium and the sterilization medium.

Optionally, each buffer container also has a sensor coupled to it, which is configured to determine a concentration of the sterilization medium in the respective buffer container. In this way, it can be ensured that the concentration of the sterilization medium is as required before it is subsequently made available for an end application.

The sterilization medium can comprise hydrogen peroxide ($H_2O_2$). Hydrogen peroxide is well suited for removing germs or bacteria from objects.

The features taught in the description and the drawings may be applied each individually or in groups in any desired combination in accordance with the disclosure.

BRIEF DESCRIPTION OF THE DRAWINGS

FIG. 2 shows a schematic representation of a method according to the disclosure for providing a sterilization medium.

DETAILED DESCRIPTION

Figure 1:
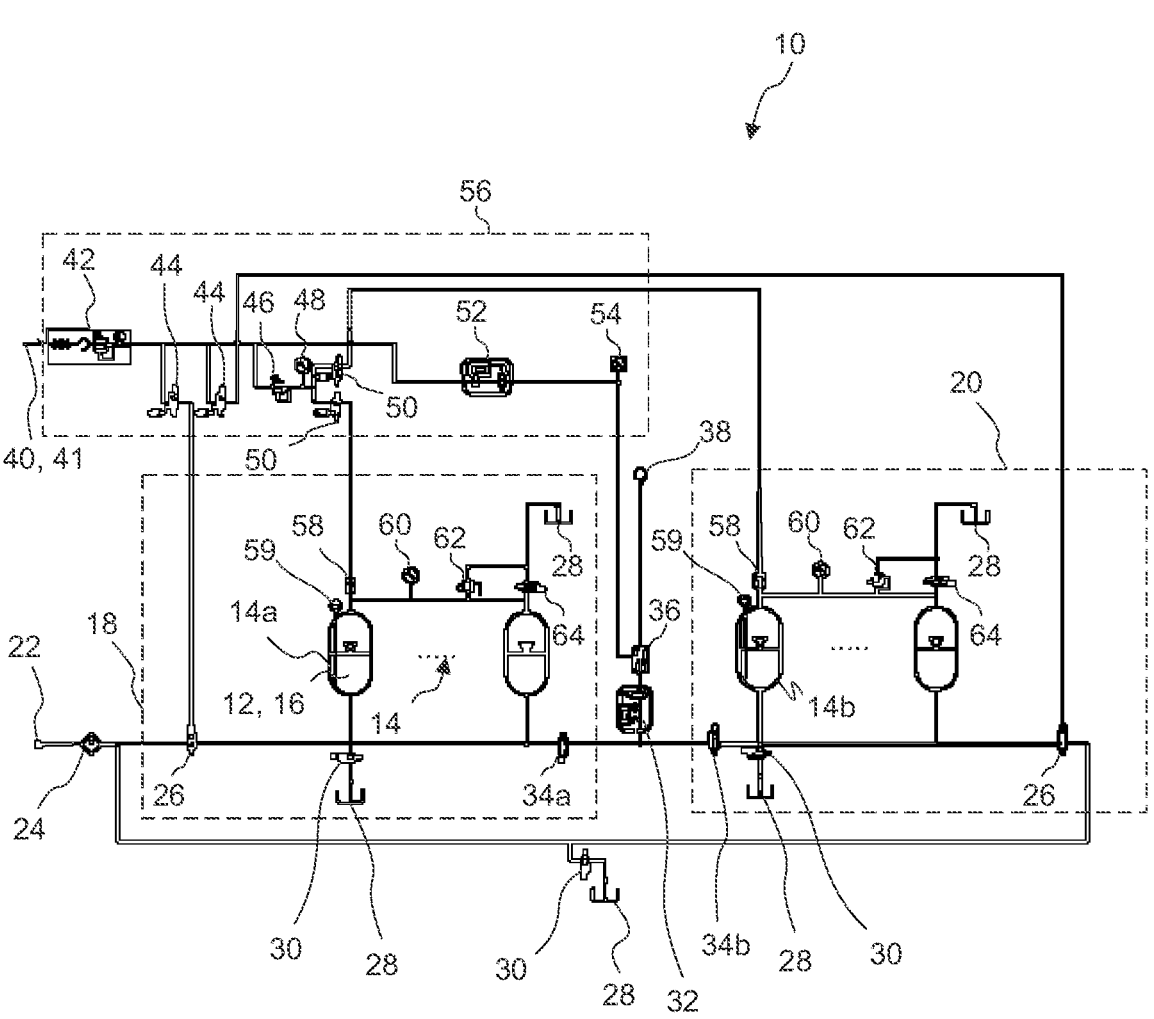
FIG. 1 shows a schematic representation of a system according to the disclosure for conveying a sterilization medium.

All of the features disclosed below with respect to the exemplary embodiments and/or the accompanying Figures may be combined alone or in any desired sub-combination with features of the aspects of the present disclosure, including features of preferred examples, provided that the resulting combination of features is useful to a person skilled in the art.

FIG. 1 shows a schematic representation of a system 10 according to the disclosure for conveying a sterilization medium 12, in this case hydrogen peroxide.

The system 10 comprises a plurality of buffer containers 14, but at least one first buffer container 14a and one second buffer container 14b.

Each buffer container 14a, 14b has a container volume 16 that is configured to store the sterilization medium 12.

The first buffer container 14a is associated with a first storage unit 18 and the second buffer container 14b is associated with a second storage unit 20 of the system 10. In the present case, each storage unit 18, 20 comprises a plurality of buffer containers 14, which is indicated by the dots. According to this embodiment, the buffer containers 14 of a storage unit 18, 20 are fluidically interconnected so that they form a respective single total volume for the sterilization medium 12 of the respective storage unit 18, 20. Generally, however, the storage units 18, 20 only need to include a single buffer container 14 each (14a, 14b in the present case).

Within the system 10, the storage units 18, 20 and the buffer containers 14a, 14b thereof are connected in parallel to each other in terms of circuit engineering.

The system 10 is coupled to a sterilization media source 22. Starting from the sterilization media source 22, the system can be filled with the sterilization medium 12. On the input side, the system 10 therefore includes a filter device 24, which is arranged between the sterilization media source 22 and the other components of the system 10. The filter device 24 is designed to remove foreign substances from the volume flow of the sterilization medium 12 starting from the sterilization media source 22.

The following technical properties of the system 10 will be discussed by reference to a single storage device 18 and a single buffer container 14 thereof, but are to be transferred accordingly to the further storage device 20 and further buffer containers 14, respectively.

A shut-off valve 26 is arranged between the filter device 24 and the buffer container 14 of the storage device 18. When the shut-off valve 26 is closed, the buffer container 14 of the storage device 18 cannot be filled with the sterilization medium 12 from the sterilization media source 22. In an open position of the shut-off valve 26, on the other hand, the process of filling the buffer container 14 is possible.

The buffer container 14 is further coupled to a drainage 28, with an additional shut-off valve 30 being arranged between the respective buffer container 14 and the drainage 28. Using the drainage 28, a buffer container 14 can be emptied, for example for maintenance purposes.

The system 10 further comprises a fluid flow controller 32. The fluid flow controller 32 is coupled to each buffer container 14 of the system 10. Respective shut-off valves 34a, 34b are arranged between the fluid flow controller 32 and the buffer container 14 of a storage unit 18, 20.

At least one of the shut-off valves 34a, 34b has a configuration that is "normally open". This means that the particular shut-off valve 34a, 34b is open in the normal case, without a respective actuating signal being applied. The actuating signal is necessary to close the shut-off valve 34a, 34b. In general, it is also possible for all shut-off valves 34a, 34b to be designed to be "normally open".

The fluid flow controller 32 is configured to provide a predetermined volume flow of the sterilization medium 12 downstream.

In the present case, the system 10 additionally comprises a generally optional dual-substance nozzle 36, which is arranged downstream of the fluid flow controller 32. The volume flow of the sterilization medium 12 provided by the fluid flow controller 32 is atomized by means of the dual-substance nozzle 36 using a carrier medium. The atomized mixture of the carrier medium and sterilization medium 12 is subsequently made available at the aerosol outlet 38 for a desired application.

The system 10 further comprises a pressure media source 40, in this case a pressure media inlet, by means of which the pressure medium 41 (in this case compressed air) is provided for the system 10.

In accordance with this embodiment, a maintenance unit 42 is also provided, which is arranged downstream with respect to the pressure media source 40. In the present case, the maintenance unit 42 comprises a ball valve, a filter device and a pressure regulating device in order to allow the provision of the pressure medium 41 within the system 10 to be controlled as required.

In addition, the pressure medium 41 is additionally used here to operate at least the shut-off valves 26. This means that the shut-off valves 26 are pneumatically operated.

For an appropriate control of the shut-off valves 26, pilot valves 44 are therefore provided, which in the present case are in the form of 3/2-way valves and are coupled to the pressure media source 40. The pilot valves 44 can be used to provide an appropriate control pressure for the shut-off valves 26, so that the switching position of the respective shut-off valve 26 can be influenced.

In addition, the system 10 according to this embodiment includes a mechanical pressure regulator 46 (pressure regulating device) and a pressure gauge 48, which are coupled to the pressure media source 40. The pressure regulator 46 may also be electronic. Arranged downstream of the mechanical pressure regulator 46 are 3/2-way pressurizing valves 50 for each storage unit 18, 20, which in the present case comprise an integral proportional valve. Starting from the 3/2-way pressurizing valves 50, the pressure media source 40 is coupled to the buffer containers 14, with a respective non-return valve 58 being additionally arranged between the respective 3/2-way pressurizing valve 50 and the respective buffer container 14. The non-return valve 58 prevents a return flow of a gas or a liquid from the buffer container 14 toward the pressure media source 40.

According to this embodiment, the pressure medium 41 is not only used to generate a pressure cushion in the buffer containers 14, but also as a conveying medium during atomization with the aid of the dual-substance nozzle 36. For this reason, a mass flow controller 52 is also coupled to the pressure media source 40. Arranged downstream of the mass flow controller 52 is a pressure transmitter 54 before the pressure medium 41 is provided in the present case as a conveying medium for the dual-substance nozzle 36.

The maintenance unit 42, the pilot valves 44, the mechanical pressure regulator 46, the pressure gauge 48, the 3/2-way pressurizing valves 50, the mass flow controller 52, and the pressure transmitter 54 may generally be considered to be part of the pressure media supply device 56.

Each buffer container 14 includes a filling level meter 59, which is configured to acquire a filling level of the sterilization medium 12 within the buffer container 14.

Moreover, each buffer container 14 is coupled to a pressure gauge 60, which optionally includes a pressure transmitter. Furthermore, each buffer container 14 has a mechanical pressure relief valve 62 coupled thereto, which ensures a safety functionality. In addition, also provided is a respective electrical pressure relief valve 64, with the mechanical pressure relief valve 62 being arranged in parallel thereto. Downstream of the mechanical pressure relief valve 62 and the electrical pressure relief valve 64, the buffer container 14 is again coupled to the drainage 28.

Apart from the shut-off valves 26, the shut-off valves 30 may generally also be pneumatically operated.

In addition, the system includes a control device, not illustrated here, which is coupled to the valves in order to set the fill mode or the spray mode for a particular buffer container 14. This means that the control device can provide corresponding actuating signals in order to open or close valves in this way. In addition, the control device is generally also coupled to further components of the system 10, for example the filling level meters 59, the pressure gauges 48, 60, the fluid flow controller 32, the dual-substance nozzle 36, the mass flow controller 52 and the pressure transmitter 54.

FIG. 2 shows a schematic representation of a method 66 according to the disclosure for providing a sterilization medium 12. Here, the method 66 is carried out using the system 10 described above.

As already described, the system 10 comprises a first buffer container 14a and a second buffer container 14b. During operation 68 of the system 10, the spray mode 72 is always set for at least one buffer container 14. The control device is employed for this purpose.

In the spray mode 72, the pressure medium 41 can thus be introduced into a buffer container 14, in particular by means of the pressure media source 40 and the 3/2-way pressurizing valves 50, in order to ensure a pressure cushion above a quantity of the sterilization medium 12. The pressure of the pressure cushion is regulated by the control device here, which can ensure an appropriate control loop on the basis of the pressure regulator 46, the 3/2-way pressurizing valve 50 and an optional proportional valve.

Since the respective buffer container 14, provided that the spray mode is set for it, is fluidically coupled to the fluid flow controller 32 with respect to the sterilization medium 12 (the respective shut-off valve 34 is then open), the pressure cushion provided allows the sterilization medium 12 to be conveyed.

For the other buffer container 14, the fill mode 70 is then set. In fill mode 70, the shut-off valve 34 is closed for the respective buffer container 14. Furthermore, the respectively associated 3/2-way pressurizing valve 50 is also closed. The shut-off valve 26, in contrast, is open. The buffer container 14 is then fluidically coupled to the sterilization media source 22. In this case, at least the electrical pressure relief valve 64 is additionally open for the respective buffer container 14. Consequently, atmospheric pressure prevails in the buffer container 14. The filling process can then advantageously be carried out against atmospheric pressure.

In a first configuration (solid arrows 74), the spray mode 72 is set for the first buffer container 14a and the fill mode 70 is set for the second buffer container 14b. When the level of the sterilization medium in the first buffer container 14a falls below a predefined threshold value, the setting is changed.

According to the second configuration (dashed arrows 76), the spray mode 72 is then set for the second buffer container 14b and the fill mode is set for the first buffer container 14a.

In this way, it can be ensured that the spray mode 72 is always set for at least one buffer container 14 during operation 68 of the system 10. To this end, the aforementioned control device is used, by means of which the valves can be controlled and switched in accordance with requirements.

In the present application, reference may be made to quantities and figures or numbers. Unless expressly indicated, such quantities and numbers should not be regarded in a limiting sense, but as examples of the possible quantities or numbers in the context of the present application. In this context, the term "plurality" may also be used in the present application to refer to a quantity or number. In this context, the term "plurality" means any number greater than one, e.g., two, three, four, five, etc. The terms "about", "approximately", "near", etc. mean plus or minus 5% of the value indicated.

Advantageous further configurations are given in the dependent claims and in the description, each of which may separately or in (sub)combination illustrate aspects of the disclosure. Individual aspects of the disclosure are discussed in relation to devices, others in relation to methods. However, the aspects are each mutually transferable accordingly.

The invention claimed is:

1. A system for conveying a sterilization medium, comprising at least two buffer containers arranged so as to be connected in parallel, for storing the sterilization medium, at least one fluid flow controller, to which each of the buffer containers is fluidically coupled, and a pressure media supply device, which couples a pressure medium source to the buffer containers and is adapted to act upon the buffer containers with a pressure medium, wherein the system is configured such that for each buffer container a fill mode and a spray mode can be set, wherein in the fill mode the correspondingly switched buffer container is adapted to be filled with the sterilization medium from a supply device and in the spray mode it is fluidically coupled to the fluid flow controller, and the sterilization medium can be conveyed from this buffer container toward the fluid flow controller based on a pressure applied by the pressure medium, and wherein the buffer containers are adapted to be switched alternately, so that while one container is in the spray mode, the other or another buffer container is in the fill mode.

2. The system according to claim 1, wherein atmospheric pressure prevails in the buffer container for which the fill mode is set.

3. The system according to claim 1, wherein each buffer container is coupled to a respective mechanical or electronic pressure measuring device to determine the fluid pressure within the buffer container.

4. The system according to claim 1, wherein each buffer container includes at least one filling level meter.

5. The system according to claim 1, wherein the system further includes a mechanical or electronic pressure regulating device that is coupled at least to the buffer containers and to the pressure media supply device and is configured to act upon each buffer container with a predefined pressure based on the pressure medium.

6. The system according to claim 5, wherein for each buffer container the system includes a proportional valve between the pressure regulating device and the buffer containers.

7. The system according to claim 1, wherein each buffer container is coupled to at least one respective pressure relief valve.

8. The system according to claim 1, wherein a non-return valve is arranged between each buffer container and the pressure media supply device such that a return flow from the buffer container into the pressure media supply device is inhibited.

9. The system according to claim 1, wherein the system further includes at least one dual-substance nozzle which, starting from the fluid flow controller, is adapted to be acted upon with the sterilization medium and additionally with a conveying medium, and is configured to atomize the sterilization medium by the conveying medium.

10. The system according to claim 1, wherein for each buffer container the system further includes a purging device that is configured to purge the respective buffer container with a cleaning agent.

11. The system according to claim 1, wherein each buffer container has an outlet line leading to a common line to the fluid flow controller, wherein shut-off valves which are closed in the fill mode are provided in the outlet lines.

12. A method of providing a sterilization medium by means of a system according to claim 1, wherein, if the fill mode is set for a buffer container, this buffer container is filled with the sterilization medium from a supply device, wherein, if the spray mode is set for a buffer container, this buffer container is acted upon with the pressure medium starting from the pressure media supply device such that a pressure is generated in the buffer container, this buffer container is fluidically coupled to the fluid flow controller and, based on the pressure generated by the pressure medium within the buffer container, sterilization medium is conveyed from this buffer container toward the fluid flow controller, and wherein, during operation of the system, the system can be switched such that the spray mode can always be set for at least one buffer container.

* * * * *